(12) United States Patent
Halpert et al.

(10) Patent No.: US 12,064,541 B2
(45) Date of Patent: *Aug. 20, 2024

(54) METHOD AND SYSTEM TO PROTECT KIDNEYS DURING SURGERY

(71) Applicant: CARDIORENAL SYSTEMS, INC., Milford, MA (US)

(72) Inventors: Andrew Halpert, Milford, MA (US); Per Ulrich, Volketswil (CH)

(73) Assignee: CARDIORENAL SYSTEMS, INC., Milford, MA (US)

(*) Notice: Subject to any disclaimer, the term of this patent is extended or adjusted under 35 U.S.C. 154(b) by 535 days.

This patent is subject to a terminal disclaimer.

(21) Appl. No.: 17/138,215

(22) Filed: Dec. 30, 2020

(65) Prior Publication Data

US 2021/0113754 A1    Apr. 22, 2021

Related U.S. Application Data

(62) Division of application No. 15/712,764, filed on Sep. 22, 2017, now Pat. No. 10,881,774.

(Continued)

(51) Int. Cl.
*A61M 5/168* (2006.01)
*A61B 5/00* (2006.01)
(Continued)

(52) U.S. Cl.
CPC ........... *A61M 1/1603* (2014.02); *A61B 5/208* (2013.01); *A61B 5/4836* (2013.01);
(Continued)

(58) Field of Classification Search
CPC .............. A61M 5/16895; A61M 5/142; A61M 5/1723; A61B 5/201; A61B 5/208
See application file for complete search history.

(56) References Cited

U.S. PATENT DOCUMENTS

| 4,291,692 A | 9/1981 | Bowman et al. |
| 5,891,051 A | 4/1999 | Han et al. |

(Continued)

FOREIGN PATENT DOCUMENTS

WO    2005/102441    11/2005

OTHER PUBLICATIONS

Loop Diuretics in Clinical Practice. Se Won Oh, et al. Electrolyte Blood Press. Jun. 2015, 13(1): 17-21. (Year: 2015).*

(Continued)

*Primary Examiner* — Laura A Bouchelle
(74) *Attorney, Agent, or Firm* — Nixon & Vanderhye P.C.

(57) ABSTRACT

A method to protect kidneys of a patient undergoing cardiac surgery patient including: administrating a diuretic to the patient to increase urine output of the patient during cardiac surgery, wherein the diuretic is administered during the cardiac surgery; anesthetizing the patient with a general anesthetic during the cardiac surgery; infusing an intravenous liquid into the patient during the cardiac surgery; monitoring a rate or amount of urine output of the patient during the cardiac surgery, and automatically adjusting a rate or amount of the intravenous liquid infused into the patient to achieve or exceed a target urine output during the cardiac surgery.

21 Claims, 3 Drawing Sheets

Related U.S. Application Data

(60) Provisional application No. 62/398,740, filed on Sep. 23, 2016.

(51) Int. Cl.
*A61B 5/20* (2006.01)
*A61M 1/16* (2006.01)
*A61M 25/00* (2006.01)
*A61M 1/34* (2006.01)
*A61M 25/02* (2006.01)

(52) U.S. Cl.
CPC ........ *A61M 5/16804* (2013.01); *A61M 25/00* (2013.01); *A61B 2560/0266* (2013.01); *A61M 1/3441* (2013.01); *A61M 2025/0213* (2013.01); *A61M 2205/3334* (2013.01); *A61M 2230/04* (2013.01)

(56) References Cited

U.S. PATENT DOCUMENTS

| | | | |
|---|---|---|---|
| 5,980,465 A * | 11/1999 | Elgas | A61M 1/3609 604/6.11 |
| 6,010,454 A | 1/2000 | Arieff et al. | |
| 6,514,226 B1 | 2/2003 | Levin et al. | |
| 7,029,456 B2 | 4/2006 | Ware et al. | |
| 7,727,222 B2 * | 6/2010 | Da Silva | A61B 5/20 604/67 |
| 7,736,354 B2 * | 6/2010 | Gelfand | G01G 17/04 604/67 |
| 8,233,957 B2 | 7/2012 | Merz et al. | |
| 8,556,846 B2 | 10/2013 | O'Mahony et al. | |
| 9,526,833 B2 | 12/2016 | Gelfand et al. | |
| 10,537,281 B2 | 1/2020 | Thompson et al. | |
| 2006/0270971 A1 | 11/2006 | Gelfand et al. | |
| 2007/0088333 A1 | 4/2007 | Levin et al. | |
| 2008/0027409 A1 | 1/2008 | Rudko et al. | |
| 2008/0221512 A1 | 9/2008 | DaSilva et al. | |
| 2009/0054745 A1 | 2/2009 | Jennewine | |
| 2009/0062730 A1 | 3/2009 | Woo | |
| 2010/0286559 A1 | 11/2010 | Paz et al. | |
| 2011/0196304 A1 | 8/2011 | Kramer et al. | |
| 2013/0261412 A1 | 10/2013 | Reed, II | |
| 2013/0274705 A1 | 10/2013 | Burnes et al. | |
| 2014/0228755 A1 | 8/2014 | Darrah et al. | |
| 2015/0258277 A1 | 9/2015 | Halpert et al. | |
| 2018/0085510 A1 | 3/2018 | Halpert et al. | |
| 2018/0110455 A1 | 4/2018 | Chang et al. | |

OTHER PUBLICATIONS

Samira Bell et al., "Risk of Postoperative Acute Kidney Injury In Patients Undergoing Orthopaedic Surgery—Development and Validation of Risk Score adn Effect of Acute Kidney Injury on Survival: Observational Cohort Study", BMJ: 2015:351:h56391 doi: 10.1136/bmj.h5639, 9 pages.

C.S.C. Bouman et al., "Red Blood Cell Transfusion and Furosemide in Cardiac Surgery: Friend or Foe?", The Netherlands Journal of Medicine, Dec. 2012, vol. 70, No. 10, 3 pages.

O. Goren et al., "Perioperative Acute Kidney Injury", British Journal of Anaesthesia, 115(S2): ii3-ii14 (2015), 12 pages.

Sean Josephs et al., "Perioperative Risk Assessment, Prevention, and Treatment of Acute Kidney Injury", International Anesthesiology Clinics, vol. 47, No. 4, www.anesthesiaclinics.com, pp. 89-105.

Philippe Kolh, "Renal Insufficiency After Cardiac Surgery: A Challenging Clinical Problem", European Heart Journal (2009) 30, pp. 1824-1827.

Andrea Lassnigg et al., "Lack of Renoprotective Effects of Dopamine and Furosemide During Cardiac Surgery", J Am Soc Nephrol 11: pp. 97-104, 2000.

Colin Lenihan et al., "Trends in Acute Kidney Injury, Associated Use of Dialysis, and Mortality After Cardiac Surgery, 1999 to 2008", Ann Thorac Surg. Jan. 2013; 95(1): 20-28, doi: 10.1016/j.athoracsur.2012.05.131, 17 pages.

Melanie Meersch et al., "Perioperative Acute Kidney Injury: An Under-Recognized Problem", Oct. 2017, vol. 125, No. 4, www.anesthesia-analgesia.org, pp. 1223-1232.

Roderica Rui Ge NG et al., "Identification of Modifiable Risk Factors For Acute Kidney Injury After Coronary Artery Bypass Graft Surgery in an Asian Population", The Journal of Thoracic and Cardiovascular Surgery, Apr. 2014, pp. 1356-1361.

Juan Jose Olivero et al., "Acute Kidney Injury After Cardiovascular Surgery: An Overview", MDCVJ, VIII (3) 2012, debakeyheartcenter.com/journal, pp. 31-36.

Charuhas Thakar, "Perioperative Acute Kidney Injury", Advances in Chronic Kidney Disease, vol. 20, No. 1 Jan. 2013: pp. 67-75.

S. Vellinga et al., "Identfication of Modifiable Risk Factors For Acute Kidney Injury After Cardiac Surgery", The Netherlands Journal of Medicine, Dec. 2012, vol. 70, No. 10, pp. 450-454.

Eiko Furutani et al., "An Automatic Control System of the Blood Pressure of Patients Under Surgical Operation", International Journal of Control, Automation, and Systems, vol. 2, No. 1, Mar. 2004, pp. 39-54.

Delos Cosgrove III et al., "Automated Control of Postoperative Hypertension: A Prospective, Randomized Multicenter Study", 1989 by The Society of Thoracic Surgeons, 6 pages.

Teixeira et al., "Fluid Balance and Urine Volume are Independent Predictors of Mortality in Acute Kidney Injury", Critical Care 17:R14 (2013) 11 pages.

Kui Jin et al., "Intensive Monitoring of Urine Output is Associated With Increased Detection of Acute Kidney Injury and Improved Outcomes," Chest Journal—Original Research Critical Care, 152#5, pp. 972-979 (Nov. 2017) 8 pages.

Abraham Otero, "A New Device to Automate the Monitoring of Critical Patients' Urine Output", Hindawi Publishing Corp, BioMed Research Int'l, vol. 2014, Article ID 587593, 8 pages.

Adaptec Medical Devices, "Ongoing Access to Real-Time and Accurate Monitoring of Urine Output Could Improve Management of Critically Ill Patients," Clinical Literature Review, (2016) 8 pages.

Mayo Clinic, "Creatinine Test", Mayo Foundation for Medical Education and Research (MFMER) (downloaded Aug. 16, 2018).

Stickler et al., "A Sensor To Detect the Early Stages in the Development of Crystalline Proteus mirabilis Biofilm on Indwelling Bladder Catheters", Journal of Clinical Microbiology, Apr. 2006, p. 1540-1542.

Antonio Tricoli, "Miniaturized Bio-and Chemical-Sensors for Point-of-Care Monitoring of Chronic Kidney Diseases," Sensors 2018, 18, 942; (Mar. 22, 2018) 18 pages.

Kambiz Kalantari, "Assessment of Intravascular Volume Status and Volume Responsiveness in Critically Ill Patients," Kidney International (2013) 83, 1017-1028 (Jan. 9, 2013) 12 pages.

David Farcy, "Review: Pitfalls in Using Central Venous Pressure as a Marker of Fluid Responsiveness," Emergency Medicine. Jan. 2016;48(1):18-28, 15 pages.

Barbara Lara, "Accurate Monitoring of Intravascular Fluid Volume: A Novel Application of Intrathoracic Impedance Measures For The Guidance of Volume Reduction Therapy," IJC Heart & Vasculature, 8 (2015) pp. 47-51, 5 pages.

Vivane Conradds, "Sensitivity and Positive Predictive Value of Implantable Intrathoracic Impedance Monitoring as a Predictor of Heart Failure Hospitalizations: The SENSE-HF Trial," European Heart Journal (2011) 32, 2266-2273, 8 pages.

Sheldon Magder et al., "The Clinical Role of Central Venous Pressure Measurements", Journal of Intensive Care Medicine 22(1); 2007, 8 pages.

Se Won Oh et al., "Loop Diuretics in Clinical Practice", Electrolytes & Blood Pressure, www.ncbi.nlm.nih.gov/pmc/articles/PMC4520883, printed Mar. 25, 2019, 6 pages.

Alison Shepherd, "Measuring and Managing Fluid Balance", Nursing Times, vol. 107, No. 28, pp. 12-16 (Jul. 19, 2011) 5 pages.

Mihai Gheorghiade et al., "Current Medical Therapy For Advanced Heart Failure", American Heart Journal, Jun. 1998, pp. S231-S248.

(56) References Cited

OTHER PUBLICATIONS

Kirkwood Adams et al., Executive Summary: HFSA 2006 Comprehensive Heart Failure Practice Guideline, Journal of Cardiac Failure, vol. 12, No. 1, 2006, pp. 10-38.

"2016 ESC Guidelines For the Diagnosis and Treatment of Acute and Chronic Heart Failure—Web Addenda", European Heart Journal, doi:10.1039/eurheartj/ehw128, 17 pages.

Lu-Ping Li et al., Evaluation of Intrarenal Oxygenation by BOLD MRI at 3.0T, J Magn Reson Imaging, Nov. 2004; 20(5): 901-904. doi:10.1002/jmri.20176, 8 pages.

Kathryn Elofson et al., "Impact of Late Fluid Balance on Clinical Outcomes in the Critically Ill Surgical and Trauma Population", www.jccjournal.org, Journal of Critical Care 30 (2015) 1338-1343.

Lizette Warner, et al., "Determinations of Renal Cortical and Medullary Oxygenation Using BOLD Magnetic Resonance Imaging and Selective Diuretics", Invest Radiol. Jan. 2011; 46(1): 41-47. doi: 10.1097/RLI.0b013e3181f0213f, 18 pages.

\* cited by examiner

METHOD AND SYSTEM TO PROTECT KIDNEYS DURING SURGERY

PRIOR APPLICATIONS

This application is a divisional of U.S. patent application Ser. No. 15/712,764 (now U.S. Pat. No. 10,881,774), filed Sep. 22, 2017, and claims the benefit of U.S. Provisional Application 62/398,740 filed Sep. 23, 2016, wherein these applications are entirely incorporated by reference.

FIELD OF THE INVENTION

The field of the invention is surgery. The invention relates to protecting a patient's kidneys during surgery, such as cardiac surgery.

BACKGROUND OF THE INVENTION

Cardiac surgery often leads to increased stress on the kidneys and in some instances can trigger acute renal injury. "Acute renal insufficiency (ARI) after cardiac surgery is a complex and frequent clinical problem. It increases short- and long-term mortality, the incidence of post-operative complications such as respiratory infections, sepsis, and gastrointestinal bleeding, and intensive care unit (ICU) and hospital lengths of stay." Kolh, "RENAL INSUFFICIENCY AFTER CARDIAC SURGERY: A CHALLENGING CLINICAL PROBLEM," EUROPEAN HEART JOURNAL, pp. 1824-1827 (9 Jul. 2009); Lenihan, "Trends in Acute Kidney Injury, Associated Use of Dialysis, and Mortality after Cardiac Surgery, 1999 to 2008," THE ANNALS OF THORACIC SURGERY, 95(1):20-8 (2013). The incidence of acute kidney injury following cardiac surgery is reported to be twenty percent (20%) of cardiac surgery patients. Thakar, "Perioperative Acute Kidney Injury," ADVANCES IN CHRONIC KIDNEY DISEASE, 20(1):67-75 (2013). "The causes of acute renal injury following cardiac surgery are numerous, and include ischemia-reperfusion injury, intra-operative dye exposure, volume depletion, atheroembolic renal insult, hemoglobinuria from hemolysis and multiple transfusions, and rhabdomyolysis from ischemic muscle injury. Olivero." "Acute Kidney Injury after Cardiovascular Surgery: An Overview," METHODIST DEBAKEY CARDIOVASCULAR JOURNAL. 8(3):31-6 (2012).

To reduce the risk of acute renal injury, it is conventional to hydrate patients by intravenous infusion of fluids before and during surgery. Hydrating a patient protects the kidneys by facilitating kidney function, promoting urine production, compensating for reduced blood pressure (due to effects of general anesthesia as a vasodilator), reducing the risk of fluid depletion in the patient, and diluting and removing nephrotoxic elements such as dyes and other wastes that may be present in the blood stream during surgery.

To avoid perioperative dehydration of the patient, the use of diuretics is typically avoided before or during cardiac surgery. In addition, already reduced intravascular pressure from vasodilation further reduces the suitability of perioperative diuretics use. Rather, there is a notion that suggests that the use of diuretics to increase urine flow during cardiac surgery is generally ineffective. Lassnigg, "Lack of Renoprotective Effects of Dopamine and Furosemide During Cardiac Surgery", JOURNAL OF THE AMERICAN SOCIETY OF NEPHROLOGY, p. 102 (2000)("Continuous infusion of renal-dose dopamine failed to exert any advantage over placebo for renal protection in well hydrated patients after cardiac surgery. Continuous infusion of furosemide not only was ineffective, but was even detrimental and induced renal dysfunction.").

Only after surgery, as the blood vessels return to their natural state, patients may be given diuretics to increase urine production, thereby removing excess fluids from the blood. Diuretics are generally administered conservatively to prevent excess urine output, as an excessive amount of fluid loss may cause the patient to become intravascularly depleted, which reintroduce the risk of acute kidney injury. Vellinga, "Identification of Modifiable Risk Factors for Acute Kidney Injury after Cardiac Surgery," THE NETHERLANDS JOURNAL OF MEDICINE, 70(10):450-4 (2012).

Despite the conventional approaches of hydrating a patient and post-surgical use of diuretics, the incidences of acute renal injury in cardiac surgery patients continue to pose a serious risk to patient health. There is a long felt need for treatments that reduce acute renal injury in cardiac surgery patients.

SUMMARY OF THE INVENTION

The inventors have conceived of and disclose herein a novel treatment to modulate kidney function to reduce the risk of acute kidney injury during surgery, such as cardiac. Generally, an increase in the kidneys function is marked by an increase in urine production and urination. The kidneys function is increased during surgery with a fluid management device that intravenously injects fluids into the patient, while monitoring urine output. A diuretic may be injected by the fluid management device or in conjunction with the operation of the device. The fluid management device adjusts the rate of fluid injection during surgery to achieve a desired balance of fluids flowing in and out of the patient. The invention allows the patient to be maintained in a fully hydrated state while the urine flow rate is maintained at artificially elevated levels during surgery. The fluid management device acts to adjust the infusion input necessary to achieve the contrary goals of a fully hydrated patient with elevated urine output.

After surgery, the fluid management device may, when used in conjunction with a diuretic, continue to monitor the urine output and facilitate the removal of excess fluid from the patient. The fluid management device may manage a negative balance between the urine output and the infused fluid to reduce the fluid volume in the patient at a gradual rate. By managing a negative balance, the fluid management system reduces the risk of dehydrating the patient, and thus further reduces the risk of acute kidney injury, while the patient is recovering from surgery.

In one embodiment, the invention is a method to protect the kidneys of a patient undergoing surgery comprising: administrating a diuretic to the patient to increase the urine output of the patient during surgery, after the patient has been anesthetized; intravenously infusing an liquid into the patient during the cardiac surgery; monitoring a rate or amount of urine output by the patient during the cardiac surgery, and adjusting a rate or amount of the intravenous liquid infused into the patient to achieve a target urine output (such as near or by at least 280 to 300 milliliters per hour) during the cardiac surgery.

In another embodiment, the invention is a method to protect kidneys of a patient undergoing cardiac surgery patient including: anesthetizing the patient with a general anesthetic; administrating a diuretic to the patient to increase urine output of the patient during cardiac surgery, wherein the diuretic is administered after the patient is anesthetized and during at least a majority (such as at least 85%) of the surgery; intravenously infusing a liquid into the anesthetized patient; monitoring a rate or amount of urine output of the anesthetized patient, and automatically adjusting a rate or amount of the intravenous liquid infused into the anesthetized patient to achieve a target urine output (such as near or at least 280 to 300 milliliters per hour) during the cardiac surgery.

In another embodiment, the invention is a method to protect kidneys of a patient undergoing cardiac surgery patient including: administrating a diuretic to the patient to increase urine output of the patient during cardiac surgery, wherein the diuretic is administered during the cardiac surgery; anesthetizing the patient with a general anesthetic during the cardiac surgery; infusing an intravenous liquid into the patient during the cardiac surgery; monitoring a rate or amount of urine output of the patient during the cardiac surgery, and automatically adjusting a rate or amount of the intravenous liquid infused into the patient to achieve a target urine output (such as at near or at least 280 to 300 milliliters per hour) during the cardiac surgery.

In another embodiment, the invention is a method to treat a cardiac surgery patient comprising: infusing an intravenous liquid into the patient during cardiac surgery; administrating a diuretic to the patient to increase the urine output of the patient, wherein the diuretic is administered during the cardiac surgery; monitoring a rate or amount of urine output of the patient; anesthetizing the patient with a general anesthetic during the cardiac surgery; automatically adjusting a rate or amount of the intravenous liquid infused into the patient to balance the patient's fluid output to achieve a target urine output (such as near or at least 300 ml/hr) during the cardiac surgery and while the patient is under the general anesthetic, and automatically adjusting the rate or the amount of the intravenous liquid infused into the patient and the urine output to achieve a urine output of near or at least 250 ml/hr but below 300 ml/hr after the anesthetizing stops and the patient becomes conscious.

In another embodiment, the invention is a method of preventing acute renal injury in a patient undergoing surgery comprising: before surgery connecting the patient to an automatic fluid balancing system which intravenously infuses an infusion fluid into the patient and which measures the patient's urine output; administrating a diuretic dose to the patient; anesthetizing the patient; performing surgery on the patient which reduces blood flow to the patient's kidneys; and reducing the oxygen demand of the patient's kidneys during and after surgery by operating the automatic fluid balancing system to infuse the patient with the infusion fluid at a rate based on the measured urine output.

In another embodiment, the invention is a console for assisting the prevention of acute renal injury in a patient undergoing surgery, wherein the console is configured to be positioned in a hospital operating room and proximate a surgical table on which lies the patient, wherein the console includes: a first weight measurement device integrated in the console configured to measure a weight of urine from the patient collected in a urine collection vessel; an infusion pump integrated with the console and configured to pump hydration fluid into the patient; and a controller integrated in the console and adapted to receive or calculate a first and second target rates of urine output for the patient, wherein the first target rate is to be applied while the patient is receiving a diuretic and undergoing a surgery and the second target rate is to be applied after the surgery, select the first or second target rate based on an input received by the controller or determination made by the controller as to whether the patient is in surgery or has completed surgery, compare the selected first or second target rate to a current rate of urine output calculated by the controller, and achieve the selected first or second target rate by automatically adjusting the infusion pump to adjust a rate of hydration fluid flowing into the patient.

The controller may be configured to automatically select the first or second target rate and both of the first and second target rates are selectively applied to the patient.

DETAILED DESCRIPTION OF THE INVENTION

Figure 1:
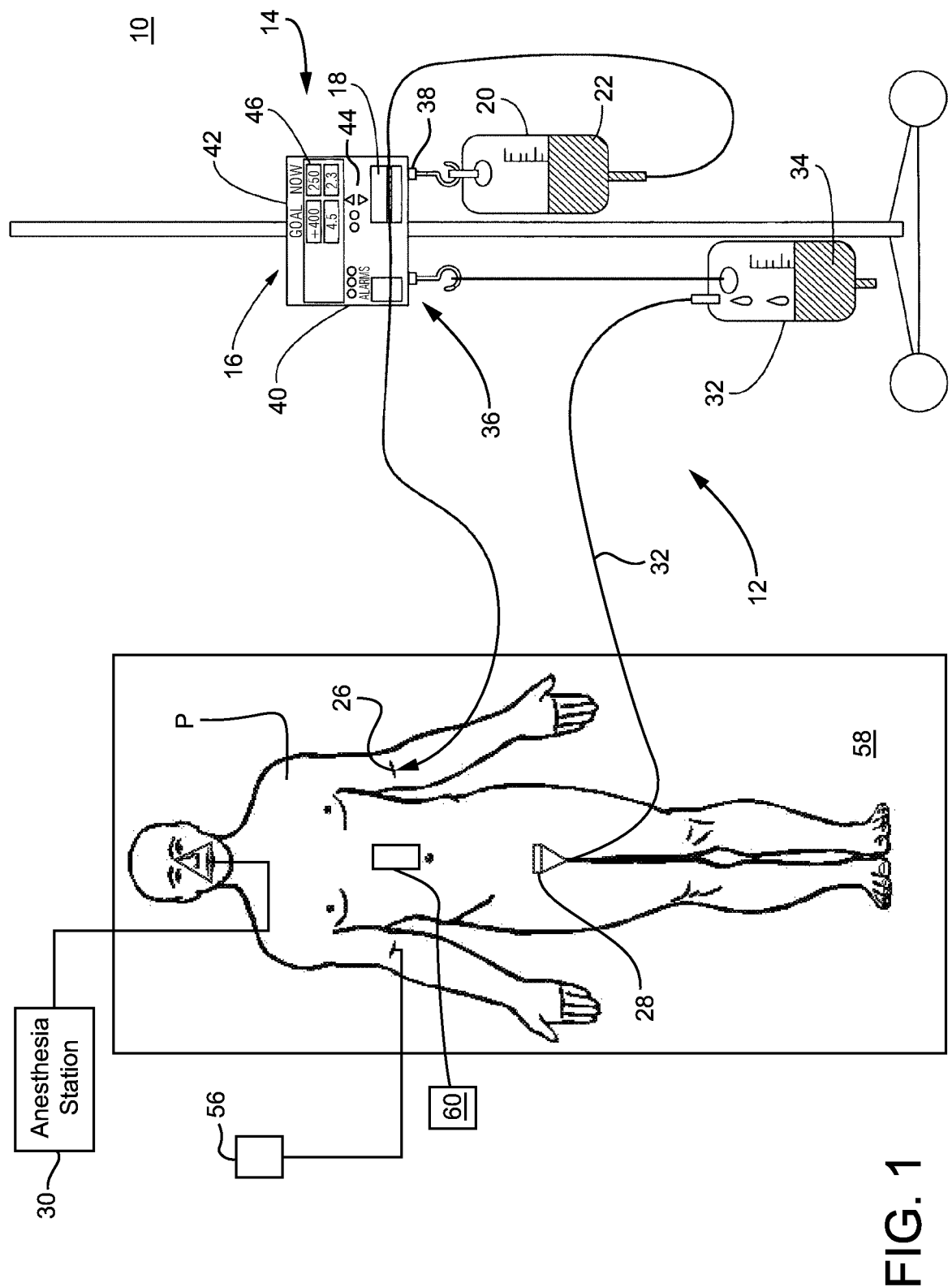
FIG. 1 is a schematic view of one embodiment of a patient hydration system which is configured to increase urine output and balance the output with fluid injected into a patient during cardiac surgery.

FIG. 1 shows a patient fluid management system 10 that includes a urine collection system 12 and a hydration fluid infusion system 14 both of which are connected to patient P being prepared for or undergoing surgery, such as cardiac which includes open heart surgery.

The hydration fluid infusion system 14 includes an infusion controller 16, that includes an infusion pump 18, e.g., a peristaltic pump, connected to a fluid source 20, e.g., saline bag, of an infusion fluid 22, e.g. saline, by tubing 24. An intravenous (I.V.) needle 26 is inserted in a vein of the patient P and is connected to infusion pump 18 via tubing 24. Fluid 22 from the source 20 flows through the tubing 24 and I.V. needle 26 directly into a blood vessel, e.g., peripheral vein, of the patient P. The amount or rate of fluid(s) 22 flowing into the patient may be determined by the pumping rate or number of rotations the infusion pump 18.

The urine collection system 12 includes catheter 28 (e.g., a Foley catheter) placed in the bladder of patient P. The catheter 28 is placed on or in the patient before cardiac surgery and before or shortly after the patient is anesthetized (as represented by anesthesia station 30) for the surgery. Tubing 32 connects catheter 28 to a urine collection device, such as a bag 32. The urine 34 collected in the bag 32 is weighed or otherwise measured by a weight scale 36 or other urine flow measurement device which communicates with the infusion controller 16. The amount or rate of urine 34 is monitored in real time by the infusion controller 16. Similarly, the amount of hydration fluid 22 in the fluid source 20 may be monitored or measured by a weight scale 38. The infusion controller 16 monitors the weight of the hydration fluid 22, the amount of the hydration fluid 22 pumped through pump 18 or otherwise monitors, in real time, the amount or rate of hydration fluid flowing into the patient P.

The fluid management system 10 may be the RenalGuard System™, developed and marketed by RenalGuard Solutions, Inc. of Milford, Massachusetts, which in the past has been used to protect patients from kidney injury during procedures that require iodinated contrast agents.

A computer control system 40 in the infusion controller 16 determines receives an input as to a desired amount(s) of urine output, such as a minimum amount of urine output, or determines for itself a desired amount or threshold urine output (such as a lower/minimum urine output) by the patient. The desired amount of urine output may be displayed on the infusion controller as a GOAL and presented next a display showing the current (NOW) urine output. The computer control system 40 monitors the rate or amount of urine output and compares it to the amount or rate of hydration fluid input. The infusion controller 16 may automatically adjusts the infusion pump 14 to control the amount or rate of hydration fluid 22 injected into the patient and this adjustment may be based on the amount or rate of urine output by the patient.

The computer control system 40 may adjust the infusion pump achieve a zero, positive, or negative net fluid balance in the patient. The fluid balance may be based on the amount of hydration fluid 22 injected into the patient as compared to the urine 34 output. A zero balance refers to injecting hydration fluid 22 at the same rate as the rate of urine 34 output or injecting an amount of fluid 22, e.g., mass, that equals the amount of urine 34 output during a certain period, such as a period of five, ten or 15 minutes. A positive balance refers to injecting more fluid 22 into the patient than the amount of urine 34 output. A negative balance refers to injecting less fluid 22 into the patient than the amount of urine 34 output.

The computer control system 40 may include a processor(s) and a non-transient memory configured to store program instructions, settings for the patient fluid management system 10 and data collected from or calculated by the computer control system 40. The data may include urine output volume or rate of urine output, amount of fluid infused into the patient and rate of infusion, the amount and rate of injection of a diuretic, the weight of the patient at various times during the infusion of the fluid, and the time during which the patient is treated with the patient fluid management system 10. The computer control system 40 may include a console 42 having a user input device 44, such as a key pad, and a user output device 46, such as a computer display.

The input device 44 may be used to input certain parameters of the treatment sessions, such as a balance level, desired urine output level, and the planned duration of the input balance level or urine output level. The desired minimum urine output alert limit may be 300 to 400 milliliters per hour (ml/hr) (or other alert limit value such as at least 280 ml/hr) during the surgery, and a lower level, such as 300 or below, e.g. 280 or 260, ml/hr for a period following the surgery. The balance levels indicate whether the amount of fluids infused into the patient should be greater or less than the patient's urine output.

The parameters, for example, may be input such that there is a desired minimum urine output of 300 ml/hr during the surgery and that a positive balance is maintained until the urine output reaches 300 ml/hr and thereafter a zero balance. The parameters may be input such that after the surgery there is a negative balance until the minimum urine output is at a reduced level that may still be above 300 ml/hr but may be lower such as in a range of 300 to 250 ml/hr. The schedule and the levels for the urine output may depend on characteristics of the patient, such as weight, susceptibility of the kidney to damage, and the diuretic used to treat the patient, and the expected period of the surgery.

A health care professional, such as an anesthesiologist, may input the settings for a treatment session using the patient fluid management system 10 into the user input 44. The computer controller 40 of the patient fluid management system 10 may be programed to apply a treatment session during which fluid 22 is infused into the patient and the rate of infusion is determined by the system based on the patient's urine 34 output and settings for the treatment session. The treatment session may start after the patient is anesthetized and before surgery.

The health care professional may monitor the treatment session by viewing the output of the display screen 46, which presents information regarding the treatment session, such as urine output level or rate, whether the fluid infusion is in a positive, zero or negative condition, and the amount of time of the treatment session. The health care professional may adjust the treatment session using by inputting setting changes into the user input 38. For example, the health care professional may adjust the treatment session to cause a high urine output, e.g., 300 ml/hr or greater, during the surgery and, after the surgery, set the system for a negative balance to remove excess fluid in the patient that was infused during surgery. The computer controller 40 may issue audible or visible alarms 29 or other information indicating whether the urine output is within or beyond the desired settings.

Figure 2:
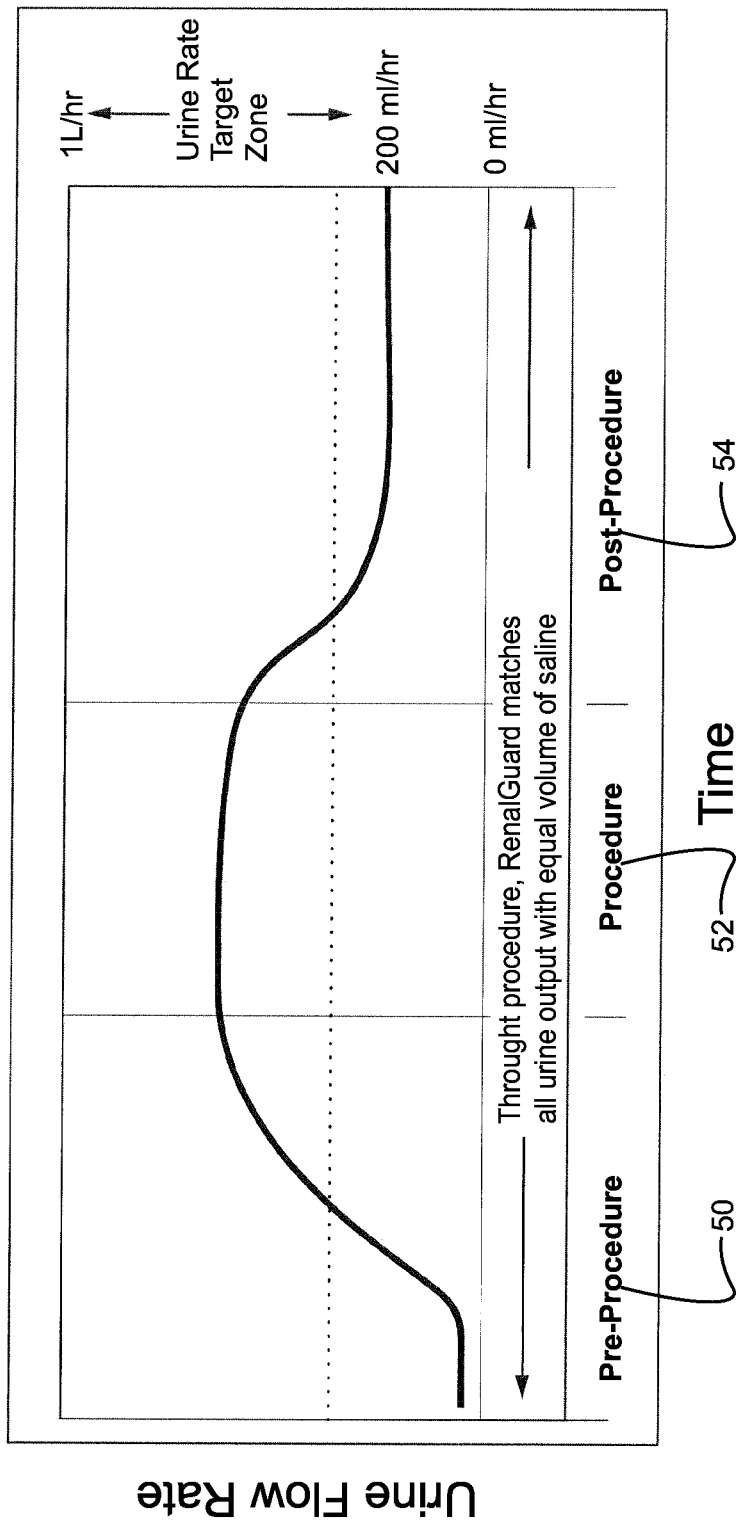
FIG. 2 is a graphical representation showing a time line of desired urine flow rate achieved with the fluid management system before, during and after an event such as cardiac surgery.

FIG. 2 is a chart showing urine output as a function of time during pre-procedure 50, during the cardiac surgery 52 and after the surgery 54. The pre-procedure 50 may be a period of a few hours or tens of minutes, e.g., 30 to 45 minutes, during which the patient is prepared for surgery. The patient may be connected to the fluid management system 10 and fitted with a urine collection catheter 28. The patient may also be connected to a source of a diuretic 56 such that the diuretic flows at a constant rate into the patient's blood system.

The patient may be positioned on a surgical table 58 in an operating room of a hospital. The patient may be placed under a general anesthetic 30 prior to and during the cardiac surgery. A side effect of general anesthetics is that they act as a vasodilator which tends to increase the size of blood vessels in the patient. The increase in vessel size increases the available volume for blood flowing through the blood vessels and, thus, tends to reduce the pressure of the blood in the vessels. The reduction in blood pressure tends to reduce the amount of oxygen in blood that is available to the kidneys. The reduced oxygen can stress the kidneys. Infusing fluids into the patient increase the fluid volume and thus increases blood pressure and the amount of oxygen available to the kidneys.

Based on the monitoring the blood pressure in the patient during surgery, the anesthesiologist or the computer controller 40 may adjust, e.g., increase, the infusion rate of fluid 22 to counteract a drop in blood pressure. For example, the computer controller 40 may be configured to monitor blood pressure and automatically increase the rate of pumping fluid 22 into the patient if the blood pressure falls below a threshold pressure level or the rate at which the blood pressure falls is greater than a threshold rate.

The surgery may be cardiac surgery, but could be other types of surgery requiring anesthesia and particularly general anesthesia. For example, the patient may undergo cardiac surgery and be connected to a heart lung machine 60 (See FIG. 1). This machine pumps blood through the blood vessels of the patient during the surgery. The heart lung machine also oxygenates the blood.

The heart lung machine 60 operates as an artificial heart during the surgery and, thus, operates in place of the patient's heart. The pressure pulses and other conditions of the blood that are caused by a normal beating heart are not exactly reproduced by a heart lung machine. The changes in the pressure pluses and the other conditions of the blood due to the switch from the patient's heart and the heart lung machine are sensed by and affect the kidneys. These changes can also stress the kidneys during the cardiac surgery. The reduced oxygen delivery and stress of the kidneys due to the heart lung machine, cardiac surgery or other surgeries is counteracted, at least partially, by infusing fluid into the patient during surgery such that the kidneys generate an artificially high amount of urine and the patient's urine rate is high, such as exceeding 300 ml/hr.

During the pre-procedure 50, an anesthesiologist may input the parameters to the user input 44 of the computer controller 40 that determine the balance of urine 34 output and fluid 22 infusion through one or more of the pre-procedure 50, surgery 52 and post-surgery 54. The parameters inputted into the computer controller 44 may cause the system 10 to create a positive balance until the urine output exceeds a minimum threshold in a range, for example, of 300 ml/hr to 400 ml/hr and thereafter to maintain a zero balance provided that the urine output is above the minimum threshold. The system may switch between a zero balance and a positive balance to maintain the urine output above the threshold during the cardiac surgery.

By setting a positive balance while applying a diuretic, the fluid management system 10 pumps more fluid 22 into the patient than is being removed as urine 34. An effect of a positive balance is that the amount of fluid increases in the patient's blood stream. The increased fluid in the patient tends to increase the blood pressure and counteract a possible blood pressure loss due to the vasodilator effect of the anesthesia. The increased blood pressure causes the oxygen pressure level in the blood at the kidneys to increase such that there is additional oxygen available to the kidneys.

The higher blood pressure is maintained due in part to the fluid management system pumping sufficient fluid into the patient to maintain a high urine output such as a minimum threshold selected from a range of 300 ml/hr or 400 ml/hr. Once the high urine output has been reached and while it is maintained, the fluid management system may switch to a zero balance to avoid pumping in additional extra fluid into the patient. The high urine output indicates that the blood pressure is sufficient to support the kidneys, the kidneys are well oxygenated and the kidneys are functioning well. The fluid management system can automatically switch to a positive balance if the urine flow drops below a threshold or to a negative balance if the urine flow exceeds a threshold. In addition or alternative to the automatic switching between zero and negative or positive balances, the fluid management systems may issue alarms or alert that are acted upon by the anesthesiologist who manually adjusts the fluid management system.

During the post-surgery period 54, the fluid management system may be programmed to achieve a negative balance mode to reduce the amount of fluid in the patient. The system may also be programmed during post-surgery to decrease the desired urine output level. For example, the desired urine output level may be to have urine at a minimum threshold range that is high as compared to the patient's typical urine output. Such a high threshold range may be 300 ml/hr to 400 ml/hr. During post-surgery, a lower minimum threshold rate may be set such as still above 300 ml/hr or in a range of 300 to 200 ml/hr.

The console 37 is also typically equipped with the user interface. The interface allows the user to set the two main parameters of therapy: the duration of hydration and the desired end net fluid balance. The net fluid balance can be zero if no fluid gain or loss is desired. Display indicators on the console show the current status of therapy: the elapsed time and the net fluid gain or loss.

The user interface may also include alarms 29. The alarms notify the user of therapy events such as an empty fluid bag or a full collection bag as detected by the weight scale 26. In one proposed embodiment, the urine is collected by gravity. If urine collection unexpectedly stops for any reason, the system will reduce and, if necessary, stop the I.V. infusion of fluid and alarm the user. In some embodiments, the I.V. infusion may be maintained at a minimal level while the alarm 29 is active. Alternatively, the console can include the second (urine) pump (see pump 70, FIG. 2) similar to infusion pump 14. This configuration has an advantage of not depending on the bag height for drainage and the capability to automatically flush the catheter 20, if it is occluded by temporarily reversing the pump flow direction.

FIG. 2 shows the expected urine flow rate in a patient receiving fluid management with the application of a diuretic. Specifically, it is envisioned that the urine flow rate shown may apply to patient preparing to undergo cardiac surgery. Once the hydration I.V. 19 and the urinary collection (e.g. Foley) catheter 20 are inserted using standard methods, fluid management therapy is initiated in a pre-procedure 50 phase. It is envisioned that the therapy is initiated with either a bolus or continuous drip of diuretic. The urine flow rate rises in response to the diuretic dose and rises steadily. To provide optimal protection, the urine flow rate should be maximized before the surgical procedure is initiated.

In the procedure 52 phase, continuous application of diuretic may be used to maintain a urine flow rate within the target zone (i.e. rate >300 ml/hr). Throughout the procedure, the fluid management system may be set to maintain a zero, positive or negative net fluid balance in the patient. As needed, the system will match all urine output with an equal volume of saline to maintain the proper urine flow rate. Additional diuretic may be administered to the patient, as needed, to maintain a flow rate within the target zone. Once the procedure is completed, a high urine flow rate should be sustained to maximize the protective benefits against AKI. Patient urine flow should continue to be monitored for at least 4 hours following the final administration of diuretic and the hydration status of the patient should be monitored even after use of the fluid management system is discontinued, at least until the urine flow rate returns to normal or near-normal levels.

Figure 3:
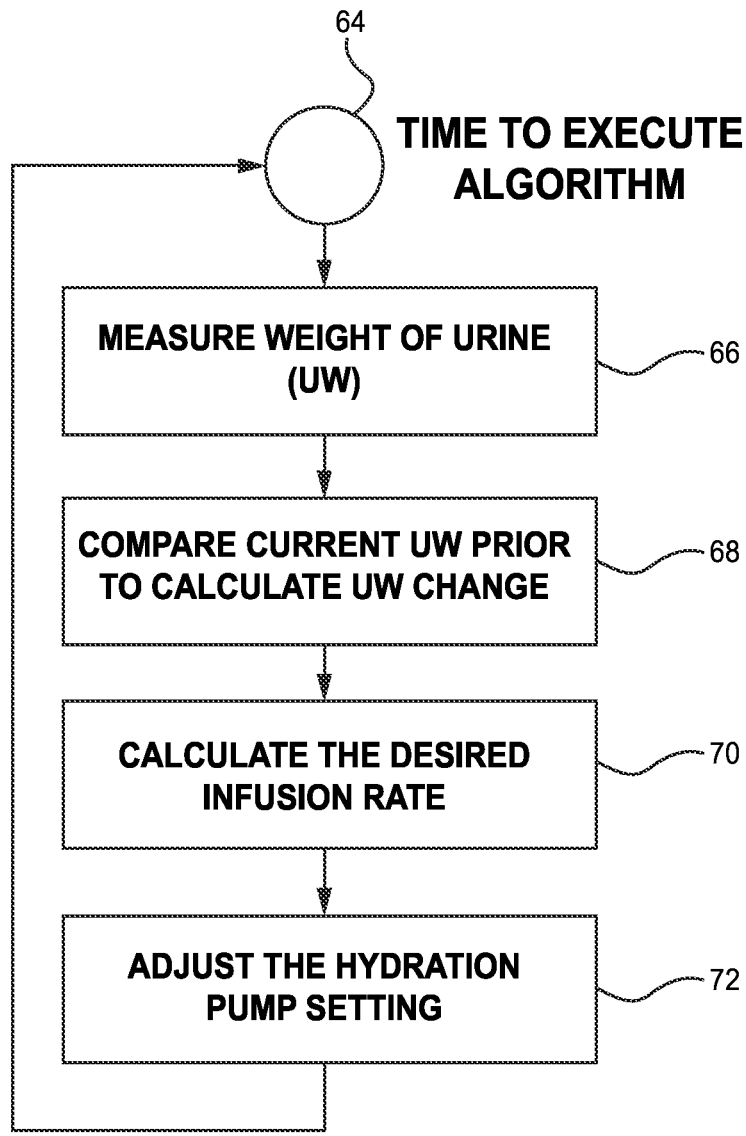
FIG. 3 is a flow chart depicting one example of the steps processed by controller and the logic used to determine and adjusting the infusion rate based on the amount of urine output by the patient.

FIG. 3 illustrates an algorithm that can be used by the controller software of the controller 44 to execute the desired therapy. The algorithm may be executed periodically 64 by the controller 44 and based on a schedule, such as performing the algorithm every thirty seconds. It is appreciated that the algorithm can be made more complex to improve the performance and safety of the device. The controller 44 is programmed to determine the rate of change of the urine 34 weight to calculate a desired infusion rate of fluid 22 based on the rate of change of the urine weight, and to adjust the hydration pump 18 settings accordingly. In step 66, the controller 44 weights the urine 34 and determines the urine output rate by comparing 68 the current weight of the urine to previous urine weight measurements. In step 70, the controller 44 calculates or otherwise determines the desired infusion rate for the fluid 22. This desired rate may be inputted to the controller 44. In step 72, the controller adjust the amount or rate of fluid 22 or the fluid pumping rate (pump 18) infused into the patient to achieve the desired infusion rate.

In at least one embodiment, the computer controller 40 (a microprocessor or microcontroller) in console 42, controls infusion pump 18 to infuse the patient with hydration fluid 22 based on the patient's urine 34 output and keeps track of the hydration fluid 22 injected in two techniques ways to provide safety and redundancy. Both the weight of hydration fluid 22 and the urine 34 output is stored by the control 40 along with the operation history of infusion pump 18. The rates or amounts of urine 34 and fluid 22 are continuously monitored and measured, such as in near real time, by the controller 40. The controller 40 may store values representing both of these measurements in a memory. If there is a difference greater than a threshold limit between the stored values and predicted values of the urine or multiple measurements of the same fluid 22 or same urine 34 values are inconsistent, an alarm signal can be generated by the controller 40 to alert a nurse or user. Controller 40 can also be programmed to output an alarm signal if, for example, the weight of saline bag 20 indicates an inconsistent or undesired level of fluid 22 compared to the pump 18 operation history. Although these condition generally arise when the saline bag is not hanging freely, the alarm signal can act as an additional safety measure to notify a nurse to check the condition of the saline bag.

Diuretic 56 administration can be performed via single bolus administration, which results in a subsequent rise in urine flow and saline infusion. Administration can also be performed using bolus administration in combination with a continuous drip. It is envisioned that this combined administration would result in an increase to urine flow and saline infusions, which would be maintained, declining from a peak level before leveling off. Once the drip is terminated, the urine flow rate is expected to decline, returning to normal levels. Finally, using only a continuous drip to administer diuretic may be preferred in some cases to most effectively reach and sustain an increased urine flow rate with corresponding saline infusion.

In one exemplary embodiment of a fluid management system, the system 10 includes a console 42, and disposable assembly of the urine collection 12 and saline infusion bag and tubing. The integrated infusion set includes an I.V. bag spike, a Luer-to-Foley connector for priming, and a urine collection set includes an integrated urine bag. The fluid management system may be the RenalGuard System™.

The power requirements for the fluid management system 10 may be 115/220 VAC, 60/50 Hz, 25 VA. An auxiliary ground post (potential equalization) and RS port are also provided for the device. When mounted on an I.V. Pole, the system requires an area of approximately 50 cm by 50 cm.

The display 46 of the fluid management system 10 may include a touch sensitive screen that may be used for both input 44 settings into the controller 44 and display information collected or generated by the controller. In an alternative embodiment, it is envisioned that tactile inputs are used to allow inputs to be performed under the encumbrance of gloves or other surgical gear.

In one aspect, a method is disclosed here for reducing or avoiding renal insult resulting from Acute kidney injury (AKI) during cardiac surgery may be comprise the steps (during the surgery) of: collecting urine 34 expelled by the patient, measuring 38 the collected urine 34 expelled, and automatically via the controller 44 infusing the patient with a fluid 22 at a rate which is a function of the measured urine expelled; and continuously administering a diuretic 56 to the patient to induce increased urine flow expelled by the patient.

Although specific features of the invention are shown in some drawings and not in others, this is for convenience only as each feature may be combined with any or all of the other features in accordance with the invention. For example, there are other ways to determine a patient's urine output and other ways to quantify the amount of hydration fluid administered to the patient. There are also other ways to redundantly check the amount of hydration fluid administered the patient. Also, the words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

The invention claimed is:

1. A method to protect kidneys of a patient undergoing open heart cardiac surgery patient including:
    anesthetizing the patient with a general anesthetic;
    administrating a diuretic to the patient to increase urine output of the patient during the open heart cardiac surgery;
    intravenously infusing a liquid into the anesthetized patient during the open heart cardiac surgery;
    monitoring a rate or amount of urine output of the anesthetized patient during the open heart cardiac surgery, and
    automatically adjusting a rate or amount of the liquid infused into the anesthetized patient to achieve at least a minimum target urine output rate or amount during the open heart cardiac surgery.

2. The method of claim 1, further comprising increasing the rate or the amount of liquid intravenously infused in response to a decrease in patient blood pressure below a certain pressure level during the open heart cardiac surgery.

3. The method of claim 1, wherein the adjusting of the rate or the amount of the liquid intravenously infused into the patient includes automatically comparing the rate or the amount of liquid intravenously infused to the rate or amount of the urine output, and automatically adjusting the rate or the amount of the liquid infused based on the comparison.

4. The method of claim 3, wherein the automatic adjusting of the rate or the amount of the liquid infused into the patient includes increasing the rate or the amount of the liquid infused to be greater than the rate or amount of the urine output until the urine output reaches the minimum target rate or amount.

5. The method of claim 1, further comprising delaying proceeding with the open heart cardiac surgery until the urine output reaches the minimum target rate or amount.

6. The method of claim 1, further comprising maintaining the rate of the liquid infused at the rate of the urine output.

7. The method of claim 1, further comprising increasing the rate or the amount of the liquid infused to above the rate or the amount of the urine output in response to the urine output falling below a certain threshold during the open heart cardiac surgery.

8. The method of claim 1, wherein the patient has been anesthetized with a general anesthetic before the administration of the diuretic and before the intravenous infusion of the liquid.

9. The method of claim 1, wherein the minimum target urine output is at rate of least 280 ml/hr.

10. The method of claim 1, wherein the urine output rate during a majority of the open heart cardiac surgery is above 300 /ml/hr.

11. The method of claim 1, wherein the minimum target urine output rate during the cardiac surgery is reduced after the open heart cardiac surgery.

12. The method of claim 1, wherein the administering of the diuretic continues at a constant rate during a majority of the open heart cardiac surgery.

13. The method of claim 1, wherein the open heart cardiac surgery is performed without an iodinated contrast agent being injected into the patient during the cardiac surgery.

14. A method to protect kidneys of a patient undergoing cardiac surgery patient including:
   anesthetizing the patient;
   administrating a diuretic to the patient to increase urine output of the patient during cardiac surgery;
   intravenously infusing a liquid into the anesthetized patient;
   monitoring a rate or amount of urine output of the anesthetized patient,
   automatically adjusting a rate or amount of the liquid infused into the anesthetized patient to achieve at least a minimum target urine output rate or amount during the cardiac surgery, and
   adjusting the rate or the amount of the liquid infused into the patient after the cardiac surgery to achieve a urine output of a second minimum urine output rate or amount which is below the urine output rate or amount used during the cardiac surgery.

15. A method to protect kidneys of a patient undergoing cardiac surgery patient including:
   anesthetizing the patient;
   administrating a diuretic to the patient to increase urine output of the patient during cardiac surgery;
   intravenously infusing a liquid into the anesthetized patient;
   monitoring a rate or amount of urine output of the anesthetized patient,
   automatically adjusting a rate or amount of the liquid infused into the anesthetized patient to achieve at least a minimum target urine output rate or amount during the cardiac surgery, and
   reducing blood flow through at least one kidney of the patient during the cardiac surgery,
   wherein the reduced blood flow reduces oxygen demand of the at least one kidney of the patient, and the minimum target urine rate is set at least 280 ml/hr, to promote an increase in the urine output of the anesthetized patient sufficiently to cause a change in the oxygen demand of the at least one kidney.

16. A method to protect kidneys of a patient undergoing open heart cardiac surgery including:
   anesthetizing the patient with a general anesthetic;
   administrating a diuretic to the patient to increase urine output of the patient during the open heart cardiac surgery;
   intravenously infusing a liquid into the patient while anesthetized and during the open heart surgery;
   monitoring a rate or amount of urine output of the patient while anesthetized, and
   automatically adjusting a rate or amount of the liquid infused into the patient while anesthetized to achieve at least a minimum target urine output rate or amount during the open heart cardiac surgery.

17. The method of claim 16, wherein the open heart cardiac surgery is performed without an iodinated contrast agent being injected into the patient during the open heart cardiac surgery.

18. The method of claim 16, further comprising bypassing the heart during the open heart cardiac surgery.

19. The method of claim 16, further comprising adjusting a rate or an amount of the liquid infused into the patient after the open heart cardiac surgery to achieve a urine output of a second minimum urine output rate or amount of urine output which is below the urine output rate or amount used during the open heart cardiac surgery.

20. The method of claim 16, further comprising:
   reducing blood flow through at least one kidney of the patient during the open heart cardiac surgery, wherein the reduced blood flow reduces oxygen demand of the at least one kidney of the patient.

21. The method of claim 16 further comprising, wherein the minimum target urine rate promotes an increase in the urine output of the anesthetized patient sufficiently to change an oxygen demand of at least one kidney in the anesthetized patient.

* * * * *